United States Patent [19]

Okioga et al.

[11] Patent Number: 5,662,915
[45] Date of Patent: Sep. 2, 1997

[54] **PESTICIDE PRODUCT DERIVED FROM THE PLANT *TAGETES MINUTA***

[76] Inventors: David Mocheo Okioga, P.O. Box 14441, Nairobi, Kenya; Ambrose Harry Rajamannan, 2120 Argonne Dr., Minneapolis, Minn. 55421

[21] Appl. No.: 382,287

[22] Filed: Feb. 1, 1995

[51] Int. Cl.⁶ .................................................. A01N 25/34
[52] U.S. Cl. ........................ 424/408; 424/409; 424/406
[58] Field of Search ........................... 424/93, 408, 409, 424/406; 435/177

[56] References Cited

U.S. PATENT DOCUMENTS

| | | | |
|---|---|---|---|
| 5,093,124 | 3/1992 | Kulenkampff | 424/406 |
| 5,248,500 | 9/1993 | Ayanaba | 424/408 |
| 5,314,814 | 5/1994 | Harder et al. | 435/177 |

*Primary Examiner*—Thurman K. Page
*Assistant Examiner*—William E. Benston, Jr.

[57] ABSTRACT

A product for killing subsurface and surface soil pathogens including nematodes, wire worms, cut worms, worms, insects, fungi and plant and soil surface pests comprises an extract derived from the plant *Tagetes minuta*. The extract may be obtained by subjecting whole or parts of the plant *Tagetes minuta* to steam distillation or the plant or plant parts may be steeped in water for a predetermined period of time to produce a liquid brew. The liquid brew may be solubilized with cellulolytic enzymes or cellulytic organisms. Solvents may also be used to solubilize the extracted brew. The extract may desicated to form a powder and the powder may be compressed to form pellets.

7 Claims, No Drawings

PESTICIDE PRODUCT DERIVED FROM THE PLANT *TAGETES MINUTA*

FIELD OF THE INVENTION

This invention relates to a product for use in killing and repelling nematodes, worms and pathogenic fungi in the soil and insects and fungi on the surface of the soil on plants.

BACKGROUND OF THE INVENTION

Pathogenic organisms such as nematodes, wire worms, cut worms, insects, fungal and bacterial pathogens residing in soils cause major economic damage to crops that are grown in such pathogen infested soils. At present, these pathogens are controlled by chemical pesticides. However, chemical pesticides are quite hazardous to farmers and the environment and will be phased out of use in the coming decade by anticipated regulations. Methyl bromide, a commonly used fumigant will be phased out in the year 2000.

Alternatives to methyl bromide and chemical insecticides are presently being researched. The alternatives being sought are those that would not be hazardous to farmers and the environment and are preferably natural products. The present invention is directed to a natural product derived from a plant which is effective as a pesticide.

SUMMARY OF THE INVENTION

An object of this invention is to provide a natural product for use in killing nematodes, worms, pathogenic fungi and insects in the soil and insects and fungi on plants which is derived from the plant, *Tagetes minuta*.

In one embodiment of the invention the product is made by steeping the whole plant including roots, stems, leaves, flowers and fruits, *Tagetes minuta* in water for one or two weeks to form a brew which when applied to the soil and the plants kills and repels various pests including nematodes. In addition to using the brewed extract as a pesticide, the extract may be desiccated, powdered or pelletized for subsequent use. In another embodiment of the invention, the steeped brew is distilled to form an oil/water liquid distillate which when applied to the soil and the plants kills various pests. The extract and/or distillates may be solubilized by a solubilizing agent including solvents for more effective use in certain conditions.

DESCRIPTION OF THE PREFERRED EMBODIMENT

The pesticide product embodying the present invention consists of the extract derived from the plant *Tagetes minuta*. This extract from *Tagetes minuta* is highly effective in killing surface as well as sub-surface pests including nematodes, wire worms, cut worms, insects, fungi. Since the extract is a natural product, i.e. derived from the plant *Tagetes minuta*, it does not pose a threat to the environment and is no danger to man.

In producing the extract, whole plants including roots, stems, leaves, flowers and fruits of the plant *Tagetes minuta*, are steeped in water for one to two weeks. The steeped brew contains the extract and may be used in treating plants to control various pests. The steeped brew may be distilled to produce an oil/water liquid distillate and this distillate may then be used in treating horticulture areas for controlling various pathogens including Root Knot nematodes which are notoriously damaging to rose plants. The steeped brew may also be subjected to steamed distillation and the volatile components may be collected as the active material. The extracted steeped brew may also be solubilized with solvents such as alcohol and the solubilized extract will be collected as the active material. Further, the extract may also be solubilized with cellulolytic enzymes or cellulolytic organisms such as bacteria and the solubilized component will be used as the active material.

Rather than steeping the whole plant and plant parts, the whole plant and parts may be compressed to squeeze the liquid from the plants which is collected as the extract. The extract may be diluted in water when applied as a pesticide. When the extract is distilled, it was found as effective as the fermented extract indicating that the active principle was thermostable since distillation at a 195° F. did not effect the activity of the extract.

The extract has been demonstrated as being highly effective in killing and repelling Root Knot nematodes for roses. The fermentated extract solution was evenly poured from a watering can to the treated areas for controlling Root Knot nematodes for roses. Treatments were repeated at two week intervals. In another manner of application, pieces of *Tagetes minuta* from which the fermentated solution was decanted were also spread on the top layer of soil and allowed to decompose.

It was found that control of Root Knot nematodes in rows or flower beds with *Tagetes minuta* extract was found to be as effective as Furodan, Nemacure and Temik. Most plants which had feeder roots destroyed by Root Knot nematodes showed a significant recovery one month after treatment of the soil with an extract from *Tagetes minuta*. Growth of plants was vigorous following control of Root Knot nematodes with the *Tagetes minuta* extract. The number and size of visible cysts on roots was reduced significantly. Normal healthy plants showing little or no symptoms of nematode infestations, were maintained with a two weekly soil drenching with *Tagetes minuta* extract throughout the five months period that trials have been in progress. It was clear that *Tagetes minuta* extract could successfully replace chemical pesticides for the control of Root Knot nematodes.

Similar experiments were conducted in the field against aphids in the soil. Experiments spraying fields and plants infested with a variety of insects and fungi showed excellent pest repelling and killing effect.

The soils to be sterilized can vary from one foot to several feet in depth. The method of infusion can be watering in, injecting in, roto tilling or shaking into the soil. The whole plant or the stem and the leaves of *Tagetes minuta* were steamed distilled and the volatile distillate was shanked or injected into the soil or watered into the soil. This infusion or injection into the soil caused the plant pathogens such as nematodes, cut and wire worms, pathogenic fungi, such as rhyzoctonia or phytopthera and insects to be killed. Further, when these preparations such as the fermentated extract or distillates were sprayed on plants infected by a variety of pathogenic insects and fungi, these pests were either repelled or killed on contact.

The application of the extract can be applied to the soil over a wide thermal range. The temperature of the soil.

Below the soil or above, plant leaf and stem and flower treatments can be varied from two ounces of the distillate to 10 gallons per acre or one gallon of the of root knot nematodes with the *Tagetes minuta* extract. The number and size of visible cysts on roots was reduced significantly. Normal healthy plants showing little or no symptons of nematode infestations, were maintained with a two weekly soil drenching with *Tagetes minuta* extract throughout the five months period that trials have been in progress. It was clear that *Tagetes minuta* extract could successful replace chemical pesticides for the control of root knot nematodes.

The following example was conducted in the field:

*Tagetes minuta* plants were collected from the wild. These plants were cut into two to three inch lengths. The cut pieces were placed in 200 liter drums filled with water. Pieces of *Tagetes minuta* plants were left in the drum for seven days to ferment. After seven days, the fermented solution was decanted and used for drenching the soil for nematode control in rose plants grown in either glass houses or in the open.

The rose plants with symptoms of nematode infestations, were growing in rows on raised beds. Each row was 27 meters long and 0.5 meter wide. Ten liters of the fermented extract solutions were used to treat soil and the root areas of the plant in each rows. Rose plants which had feeder roots destroyed by Root Knot nematodes showed significant recovery one month after treatment of the soil with the extract from *Tagetes minuta*. Growth of plants was vigorous following control of Root Knot nematodes with *Tagetes minuta* extract. The number and sizes of visible cysts on roots was reduced significantly. Normal healthy plants, showing little or number and sizes of visible cysts on roots was reduced significantly. Normal healthy plants, showing little or no symptons of nematode infestations were maintained with a two weekly soil drenching with *Tagetes minuta* extract throughout the trials.

What is claimed is:

1. A product for killing subsurface and surface soil pathogens including nematodes, wire worms, cut worms, insects, fungi, and plant and soil surface pests, consisting of an extract derived from the plant *Tagetes minuta*.

2. The product as defined in claim 1 wherein said extract is produced by subjecting whole or parts of the plants *Tagetes minuta* to steam distillation, and thereafter collecting the volatile components as the active material of said product.

3. The product as defined in claim 1 wherein said extract is produced by steeping whole or parts of plants in water for a predetermined period of time to produce a liquid brew and solubilizing the liquid brew with cellulolytic enzymes or cellulolytic organisms to produce a solubilized extract.

4. The product as defined in claim 1 wherein said extract is produced by subjecting whole or parts of the plant *Tagetes minuta* in water for a predetermined period of time to produce a liquid brew, and solubilizing the liquid brew with a solvent comprising alcohol to produce a solubilized product.

5. The product as defined in claim 1 wherein the whole plants or parts of the plant of the plant *Tagetes minute* are subjected to compression to squeeze the extract from plants and plant parts to thereby produce the product.

6. The product as defined in claim 1 wherein the extract is descicated to produce a powdered product.

7. The product as defined in claim 1 wherein the extract is descicated and thereafter pelletized into pellets.

* * * * *